United States Patent [19]

Lister et al.

[11] Patent Number: 5,239,996

[45] Date of Patent: Aug. 31, 1993

[54] CONTROLLABLE NETWORK OF RELATED MEDICAL PATIENT ATTACHED DEVICES FOR COORDINATED CONTROL

[75] Inventors: John L. Lister, Miami Beach; William E. Deuter; Marcos Mantel, both of North Miami; Michael Shenkin, Cooper City, all of Fla.

[73] Assignee: North Broward Hospital District, Fort Lauderdale, Fla.

[21] Appl. No.: 788,350

[22] Filed: Oct. 6, 1991

[51] Int. Cl.$^5$ ............................................. A61N 1/08
[52] U.S. Cl. ........................................ 607/6; 128/709; 607/9
[58] Field of Search .................... 128/419 R, 709, 903, 128/904, 783, 786, 419 P, 419 D; 361/346, 350, 351

[56] References Cited

U.S. PATENT DOCUMENTS

| | | | |
|---|---|---|---|
| 3,058,458 | 10/1962 | Daneman | 128/709 |
| 4,319,241 | 3/1982 | Mount | 128/904 |
| 4,554,928 | 11/1985 | Webster, Jr. | 128/709 |
| 5,044,367 | 9/1991 | Endres et al. | 128/419 R |

Primary Examiner—Kyle L. Howell
Assistant Examiner—George Manuel
Attorney, Agent, or Firm—Malin, Haley DiMaggio & Crosby

[57] ABSTRACT

A primary central controller switch box for providing a centralized means for alternatively coupling a defibrillator, a plurality of pacers and recorders in conjunction with a quadripolar endocardial catheter, an apex and back body surface electrode, and an arterial or ventricular catheter having a means for selection therebetween. The switch box incorporates a plurality of switches allowing for manual selection of each of said instruments in predetermined combinations to eliminate the possibility of multiple support therapy and further decrease the time it takes to switch between instruments when used in a cardiac catheterization environment, electro physiological environment, cardiac resuscitation ward, ablation study, or the like clinical settings.

11 Claims, 3 Drawing Sheets

CONTROLLABLE NETWORK OF RELATED MEDICAL PATIENT ATTACHED DEVICES FOR COORDINATED CONTROL

FIELD OF THE INVENTION

The present invention is directed to an electromechanical switch box and, in particular, to a manually operated switch box used to control multiple medical instruments and their associated electrodes.

BACKGROUND OF THE INVENTION

The medical care field has come to rely upon the use of complicated instruments for obtaining data and for treating physical ailments. With the aid of these instruments, medical procedures considered too complex a decade ago are now performed on a daily basis. In certain procedures, a number of instruments are used in combination to obtain the desired results. These instruments could be combined into a single "multi-function" instrument; however, combining functions is not practical in many situations due to compatibility, independence of operation, serviceability, complexity of operation, or the combination may simply be uneconomical. A manufacturer may produce a state-of-the-art instrument that performs a particular function but may not offer a complimenting instrument required for a particular procedure. If functions are combined and one function fails, the device may be rendered inoperative. As new and improved instruments are introduced, neither physician nor patient can afford to wait until a multi-function device is created that incorporates the new technology.

Whatever reason is given for not combining instruments, some medical procedures are adversely affected by the lack of such a device, particularly cardiac catheterization environments, electro physiological environments, cardiac resuscitation wards, ablation studies clinical settings, and the like. For instance, an electrocardiogram (ECG) may be used to provide a graphic recording of the electrical manifestations of the heart action obtained from sensing devices such as electrodes placed on the patient. Typically a multi-polar endocardial catheter is inserted into the patient for accurate pick-up of the electrical impulses. The ECG provides a means for monitoring the heart to explore the condition providing an instant indication of heart stoppage or a heart in ventricular fibrillation. Both circumstances require definitive therapy to restore the heart to normal operation.

One method for repairing the heart is by use of induced electrical shock. This may be in the form of a large shock to restart the heart, a plurality of smaller shocks to "pace" the heart, or an ablation to repair portions of the heart deemed to be the cause of an abnormality. Obviously, the length of time it takes to render corrective therapy can save a life. Even if all instruments involved in the procedure are compatible and use a common electrode such as the endocardial catheter, the physician must disconnect the catheter from one instrument and connect it to the device used for supportive therapy. If a body surface electrode is used in combination with or separate from the catheter, the physician will have to deal with connecting the various instruments to utilize the common electrode. If a defibrillator is required, the physician must disconnect the recorder and hook up the defibrillator. If a pacer is required, again the devices must be switched if the physician intends to use the catheter. If atrial or ventricular defibrillation is employed, again the physician may have to disconnect the electrode from one device and reconnect to another. Through all this switching, the physician is prone to improper connecting of the electrode resulting in an inverse of polarity causing improper output. To rectify this, the electrode would have to be reconnected to a proper polarity. It should be obvious that any switching or determining which instrument is connected to which catheter takes time, time which the patient can not afford.

A physician must take advantage of every instrument available and each instrument may utilize different connections. When one recorder is removed for service or replaced by an improved device having a slightly different isolating or connecting technique, the physician must spend time becoming familiar with the switching process before the device is made operational. To avoid this situation, patients may be coupled to all these instruments simultaneously which can add to the confusion making it difficult to trace the coupling origin.

The problems described above are typical of those encountered with instruments used in a cardiac catheterization environment, electro physiological environment, cardiac resuscitation ward, ablation studies, or the like clinical settings. Of all situations, it should be understood that a physician working in a clinical setting requires not only the latest in technology but also the ability to coordinate such technology. What has not been heretofore provided is a means for controlling key components of various instruments for the treatment of heart patients. As is described later in this specification, the need for such an instrument is not only a long felt need but one capable of saving lives. While efforts have been made toward resolving these problems, no satisfactory solution has heretofore been provided. It is, therefore, to the effective resolution of these problems that the instant invention is directed.

SUMMARY OF THE INVENTION

The principal object of the present invention is to provide a simple and reliable device which overcomes the problems previously described associated with instruments utilized in cardiac catheterization environments, electro physiological environments, cardiac resuscitation wards, ablation studies, clinical settings, and the like. The instant invention is a switch box for use as a traffic controller over a plurality of medical instruments associated with the procedure of ablation defibrillation. In particular the switch box controls the critical functions of a defibrillator, a plurality of Pacers, and a plurality of recorders such as electrocardiograms for use with common electrodes providing the physician with an instant ability to switch to any coupled instrument without change of electrodes.

When the switch box is coupled to a quadripolar endocardial catheter and/or a body surface electrode with an electrocardiogram, the electrocardiogram could be used to explore the heart in its conventional manner wherein the switch box allows selection of individual electrodes, polarity, or any combination thereof. If the exploration depicts a need for pacing at a particular electrode sensor, a pacer coupled to the switch box can be made operational by simply toggling a switch on the switch box. Coupling a defibrillator to the switch box provides the ability to switch to a defibrillator without change of electrodes or loss of polarity.

Ideally, all of the described instruments are coupled to the switch box wherein the switch box allows manual selection thereof in combination with said electrodes in a predetermined pattern. The instant device requires no electricity and the predetermined combinations prevents incorrect instrument combinations such as operating a pacer at the same time as a defibrillator. The switch box allows for electrode selection from one of five bipolar combinations allowing an Ablate, Pace, or Explore function mode. To initiate ablation, frontal mounted safety control switches are provided Selection of an Apex or Back body surface electrode is made possible as is the use of atrial and ventricular catheter. Means for reversing polarity of each electrode is incorporated within. In effect, the switch box has three major functional modes:

A. Ablate - which routes an external defibrillator to a multipolar endocardial catheter and/or a body surface electrode.

B. Pace - which routes to the above multipolar endocardial catheter and/or the body surface electrode pacer pulses selected from an external pacer while disabling the Ablate function.

C. Explore - route from the multipolar endocardial catheter and/or body surface electrode a signal to an external recorder disabling the Ablate and Pacer functions.

Therefore, a primary objective of the invention is to provide a centralized activating device for coupling critical equipment together in a clinical setting allowing for the correct combination thereof while effectively isolating non-essential equipment.

Still another objective of the present invention is to provide an apparatus for utilizing common electrodes for multiple purposes.

Yet still another objective of the present invention is to provide a single control box that can be coupled to a plurality of existing patient monitoring and stimulating devices reducing dependency upon learning particularities of each device.

Another object of the present invention is to provide a controllable network of medical devices connected to a patient for coordinating the monitoring and administering of patient stimulation comprising: a defibrillator, a plurality of pacers, a plurality of recorders, a quadripolar endocardial catheter, a body surface electrode, an atrial catheter, a ventricular catheter, and a switch box, whereby said switch box is coupled to and networks each of said medical devices for coordinating the monitoring and administering of patient stimulation.

Other objects and advantages of this invention will become apparent from the following description taken in conjunction with the accompanying drawings wherein are set forth, by way of illustration and example, certain embodiments of this invention. The drawings constitute a part of this specification and include exemplary embodiments of the present invention and illustrate various objects and features thereof.

BRIEF DESCRIPTION OF THE DRAWINGS

The invention will be more readily understood with reference to the accompanying drawing, wherein.

DETAILED DESCRIPTION OF THE INVENTION

As required, detailed embodiments of the present invention are disclosed herein, however, it is to be understood that the disclosed embodiments are merely exemplary of the invention which may be embodied in various forms. Therefore, specific functional and structural details disclosed herein are not to be interpreted as limiting, but merely as a basis for the claims and as a representative basis for teaching one skilled in the art to variously employ the present invention in virtually any appropriately detailed structure.

The switch box requires no external electrical source and has three main functions:

a. Ablate which is used to route an electrical pulse as generated by an external defibrillator to a multipolar endocardial catheter and or a body surface electrode.

b. Pace which is used to route electrical pulses as generated by an external pacer to a multipolar endocardial catheter and or a body surface electrode.

c. Explore is used to route electrical pulses as generated by the human heart to an external ECG recorder.

Figure 1:
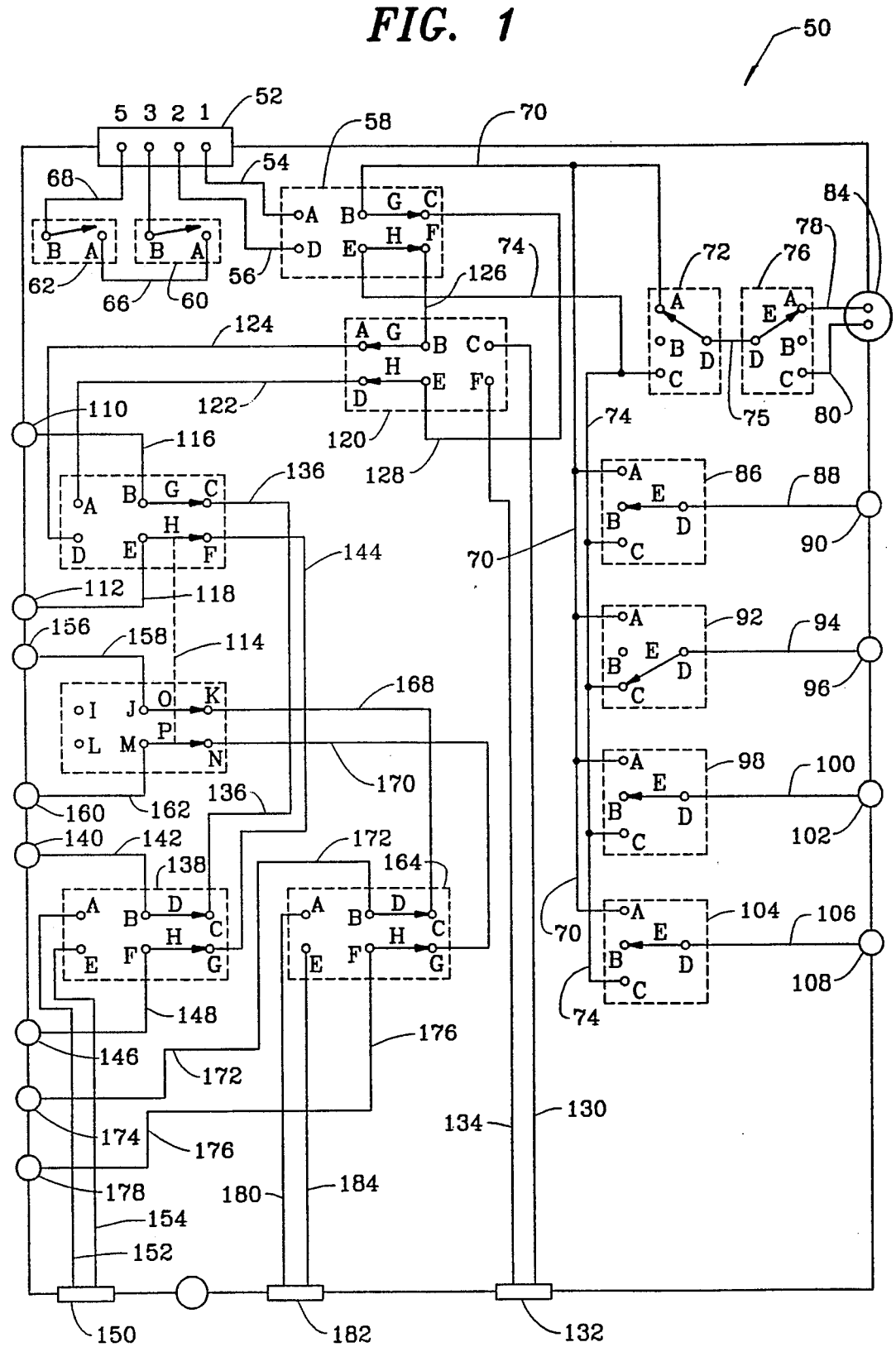
FIG. 1 is an electrical diagram of the switch box.

Now referring to FIG. 1, the electrical schematic of the ablation switch box 50 includes a defibrillator jack 52 for coupling to an external defibrillator such as the HEWLETT PACKARD (HP) 43100A, having polarity wires 54 and 56 from HP pin 1 and 2 to a Defibrillator/Pace-Explore panel mounted DPDT toggle switch 58 poles 58A & 58D respectfully. To ablate requires use of separate and independent push button switches 60 and 62 as a safety mechanism requiring a hand push to operate thus completing an external circuit between pin 3 and pin 5 of the HP Defibrillator. Ablate mode of switches 60 and 62 connects push button 60 at pole 60a and from pole 60b to push button 62 by wire 66 to 62a and from 62b to HP pin 5 by wire 68. Defibrillator mode of switch 58 connects 58a and 58b by throw 58c and by wire 70 to pole 72a of SPST panel mounted toggle switch 72. Defibrillator mode of switch 58 further connects 58d and 58e by throw 58h and by wire 74 to pole 72c of SPST panel mounted toggle switch 72. Switch 72 is in effect a polarity selector for coupling the switch box to a conventional body surface electrode by wire 75 connecting pole 72d to body surface electrode selector panel mounted SPST toggle switch 76 at pole 76D. Switch 76 permits connection to an apex body surface electrode (not shown) when throw 76e connects pole 76d to 76a and by wire 78 to Twinax Jack mount 84. Alternatively, switch 76 permits connection to a back body surface electrode (not shown), when throw 76E connects pole 76D and 76C and by wire 80 to Twinax Jack mount 84. From the diagram, it should be evident that switch 72 will allow for a correction of polarity to either electrode by use of switch 72. This is especially important when using multi-purpose electrodes by saving time of reversing polarities for correct operation of recorders and display devices. Switch 76 can be placed neutral by positioning throw 76e to pole 76b for disabling body surface electrodes or (BSE).

In similar fashion to the BSE, a quadripolar endocardial catheter, not shown, is coupled to the switch box 50. In particular, wire 70 is connected to a first catheter panel mounted SPST toggle switch 86 at pole 86A. Wire 74 is connected to a first sensor by pole 86C. As shown, the first sensor is disabled by placement of throw 86E to pole 86B. If wire 70 was polar and the first sensor was to be used in a similar mode, placement of throw 86E to pole 86A completes the circuit to pole 86D which is coupled to wire 88 and pin jack 90. If a reverse polar first sensor is desired then placement of throw 86E to pole 86C connects reverse polar wire 74 to pole 86D which is coupled to wire 88 and pin jack 90.

Wire 70 is further connected to a second sensor panel mounted SPST toggle switch by pole 92A. Wire 74 is connected to the second sensor by pole 92C. If wire 70 is polar and the second sensor is used in a similar polar mode, placement of throw 92E to pole 92A completes the circuit to pole 92D which is coupled to wire 94 and pin jack 96. To disable the second sensor, placement of throw 92E to pole 92B isolates the circuit. If reverse polar second sensor is desired, placement of throw 92E to pole 92C completes the task.

Wire 70 is further connected to a third sensor by panel mounted SPST toggle switch 98 by pole 98A. Wire 74 is connected to the second sensor by pole 98C. As shown, the second sensor is disabled by placement of throw 98E to pole 98B. If wire 70 was polar and the third sensor was to be used in a similar polar mode, placement of throw 98E to pole 98A completes the circuit to pole 98D which is coupled to wire 100 and to pin jack 102. If a reverse third sensor is desired then placement of throw 98E to pole 98C completes the circuit to pole 98D which is coupled to wire 100 and pin jack 102.

The first sensor of the quadripolar catheter is further connected by wire 70 to panel mounted SPST toggle switch 104 at pole 104A. Wire 74 is connected to the fourth sensor by pole 104C. As shown, the first sensor is doubled by placement of throw 104E to pole 104B. If wire 70 was polar and the fourth sensor was to be used in a similar polar mode, placement of throw 104E to pole 104A completes the circuit to pole 104D which is coupled to wire 106 and pin jack 108. If a reverse polar sensor is desired then placement of throw 104E to pole 104C completes the circuit to pole 104D which is coupled to wire 106 and pin jack 108.

Switch box 50 can be coupled to one or more Pacers. A first Pacer, not shown, such as a MEDTRONIC Pacemaker (5330/5375) is connected to polar pin jack 110 and reverse polar pin jack 112. It should be noted that incorrect coupling of polarity can be corrected by electrode polarity switches. Pin jack 110 is connected to pole 114B of panel mounted 4PDT toggle switch 114 by wire 116. Pin jack 112 is connected to pole 114E of panel mounted 4PDT toggle switch 114 by wire 118. Switch 114 selects between use of the previously mentioned body surface electrode (BSE) and associated quadripolar electrodes and a Pace Atrial and Ventricular Catheters described later in this specification. When the BSE and/or quadripolar electrodes are selected, throw 114G connects 114B to 114A which in turn is connected to pole 120D of switch 120 by wire 122. Likewise throw 114H connects 114E to 114D which in turn is connected to pole 120A of switch 120 by wire 124. Switch 120 is a panel mounted DPDT toggle switch for selection of Pacer to said electrodes or for coupling said electrodes to an exploring device such as an ECG and the like as illustrated. By closing throw 120G, 120A is connected to 120B, and wire 126 is connected to 58F of switch 58. Likewise throw 120H is connected to 120F and wire 128 is connected to 58C of switch 58. Placement of switch 120 in the Explore mode causes throw 120g to connect pole 120B to 120C which is connected by wire 130 to a jack 132. In addition, the Explore mode connects poles 120E and 120F by throw 120H and to jack 132 by wire 134. The recorder or display device can be coupled to jack 132.

Alternatively, the first Pacer can pace other catheters by toggling switch 114, as illustrated, whereby throw 114G connects pole 114B to 114C to wire 136 which is directed to panel mounted DPDT switch 138 pole 138C for coupling to an Atrial Catheter not shown. Throw 138D connects pole 138C to pole 138B which in turn connects to pin jack 140 by wire 142. Pole 114E is connected to pole 114F by throw 114H to wire 144 and further to pole 138G which is connected to pole 138F by throw 138H and to jack 146 by wire 148. As previously mentioned, a means for obtaining data from the Atrial Catheter can be performed by coupling a recorder to jack 150, which is connected to pole 138A of switch 138 by wire 152 and pole 138E of switch 138 by wire 154. Recording is accomplished by placement of throw 138D and 138H in the alternate position connecting to 138A and 138E respectfully.

A second Pacer, not shown, can be coupled to the switch box 50 for pacing of a Ventricular Catheter or recording therefrom. Pin jack 156 is connected to pole 114J of panel mounted 4PDT toggle switch 114 by wire 158. Pin jack 160 is connected to pole 114M of panel mounted DPDT toggle switch 114 by wire 162. Poles 114I and 114L are not connected so that when switch 114 is operated for use of the first Pacer in operating the BSE and associated electrodes, the second Pacer will be non-functional. However, when the first Pacer is switched by 114 to allow operation of the atrial catheter the second Pacer is switched simultaneously allowing connection of the second Pacer to a Ventricular catheter not shown. Placement of throw 114O connects 114J to 114K which in turn is coupled to pole 164C of switch 164 by wire 168. Pole 114M is connected to pole 114N by throw 114P which in turn is Coupled to pole 164G of switch 164 by wire 170. In a similar fashion to the Atrial Catheter, the Ventricular Catheter may be used for pacing or used for sensing of data, switch 164 allows the physician to chose which mode. As illustrated, the second Pacer is coupled to the Ventricular Catheter by throw 164D connecting pole 164C to 164B which in turn is connected to wire 172 and jack 174. Pole 64G is therefore also connected by throw 164H to pole 164F to wire 176 and jack 178. A recorder, not shown, can be used to obtain data from the Ventricular Catheter by toggling switch 164 whereby pole 164A would connect to pole 164B by throw 164D to wire 180 to jack 182, and pole 164E is connected to pole 164F by throw 164H to wire 184 and jack 182 for coupling to the recorder.

Figure 2:
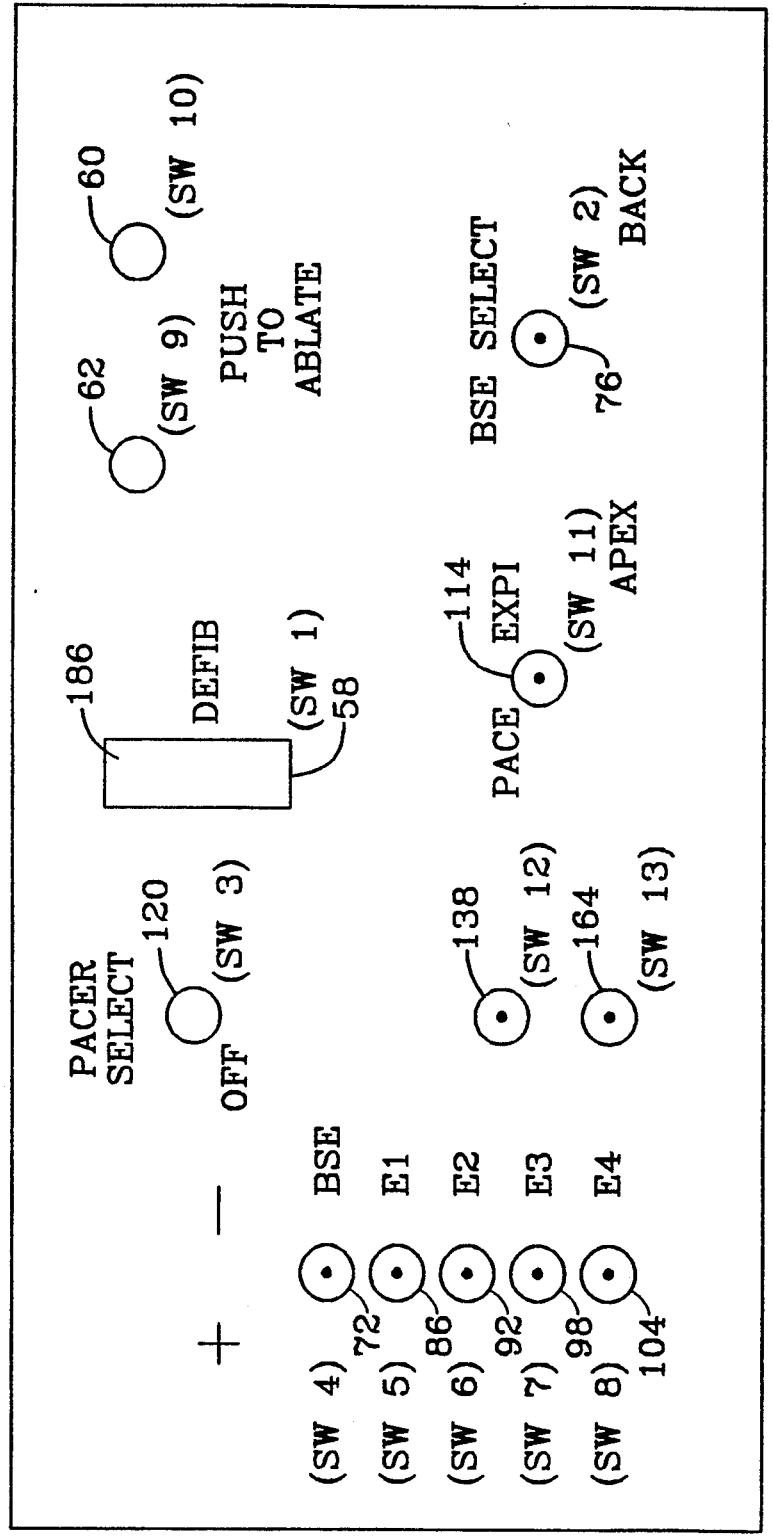
FIG. 2 is a front view of the switch box apparatus.

Now referring to FIG. 2, the front view of the switch box is depicted illustrating the simplistic array of switches for control of the switch box. In coordination with the schematic of FIG. 1, switch 72 is provided for reversing polarity and enabling of the BSE electrode, switch 86 is for the first sensor of the quadripolar electrode switch 92 is for the second sensor, switch 98 for the third sensor, and switch 104 for the fourth sensor. Switch 76 selects between use of the Apex or Back BSE. Switch 114 selects between use of the BSE or Atrial and Ventricular catheters by switch 138 for pacing to the Atrial catheter or recording therefrom. Switch 120 selects use of the BSE and associated electrodes for pacing or for exploring purposes. Switch 58 is a safety switch requiring a physical lifting of a protective cover 186 thereby disabling the Pacer/Exploring functions and making the BSE and associated electrodes available for ablation. In the Ablate mode, push button 60 and 62 must be physically pushed to perform the function. Operation is as follow:

A. To Ablate:
1. Remove guard on SW 1;
2. Select "Defib" position on SW 1;
3. Select BSE (Apex or Back) on SW 2;
4. Select any combination of electrodes (BSE,E1,E2,E3,E4) by means of switches 4,5,6,7,8 to obtain bipolar configuration;
5. Depress switches SW 9 and SW 10 simultaneously.
B. To Pace Multipolar Catheter:
1. Select "Pace/Expl" position on SW 1;
2. Select "Pace" position on SW 3;
3. Select BSE (Apex or Back) on SW 2;
4. Select any combination of electrodes (BSE,E1,E2,E3,E4) by means of switches 4,5,6,7,8 to obtain bipolar configuration;
C. To Pace Atrial and Ventricular Catheters
1. Select Atrial or Ventricular on SW 11;
2. Select Pace 1 or pace 2 on SW 12 and SW 13.
D. To Explore:
1. Select "Pace/Explore" position on SW 1;
2. Select "Expl" position on SW 3;
3. Select BSE (Apex or Back) on SW 2;
4. Select any combination of electrodes (BSE,E1,E2,E3,E4) by means of switches 4,5,6,7,8 to obtain bipolar configuration;
E. To Record Arterial and Ventricular Catheters;
1. Select "Rec" on SW 12 and/or SW 13.

Figure 3:
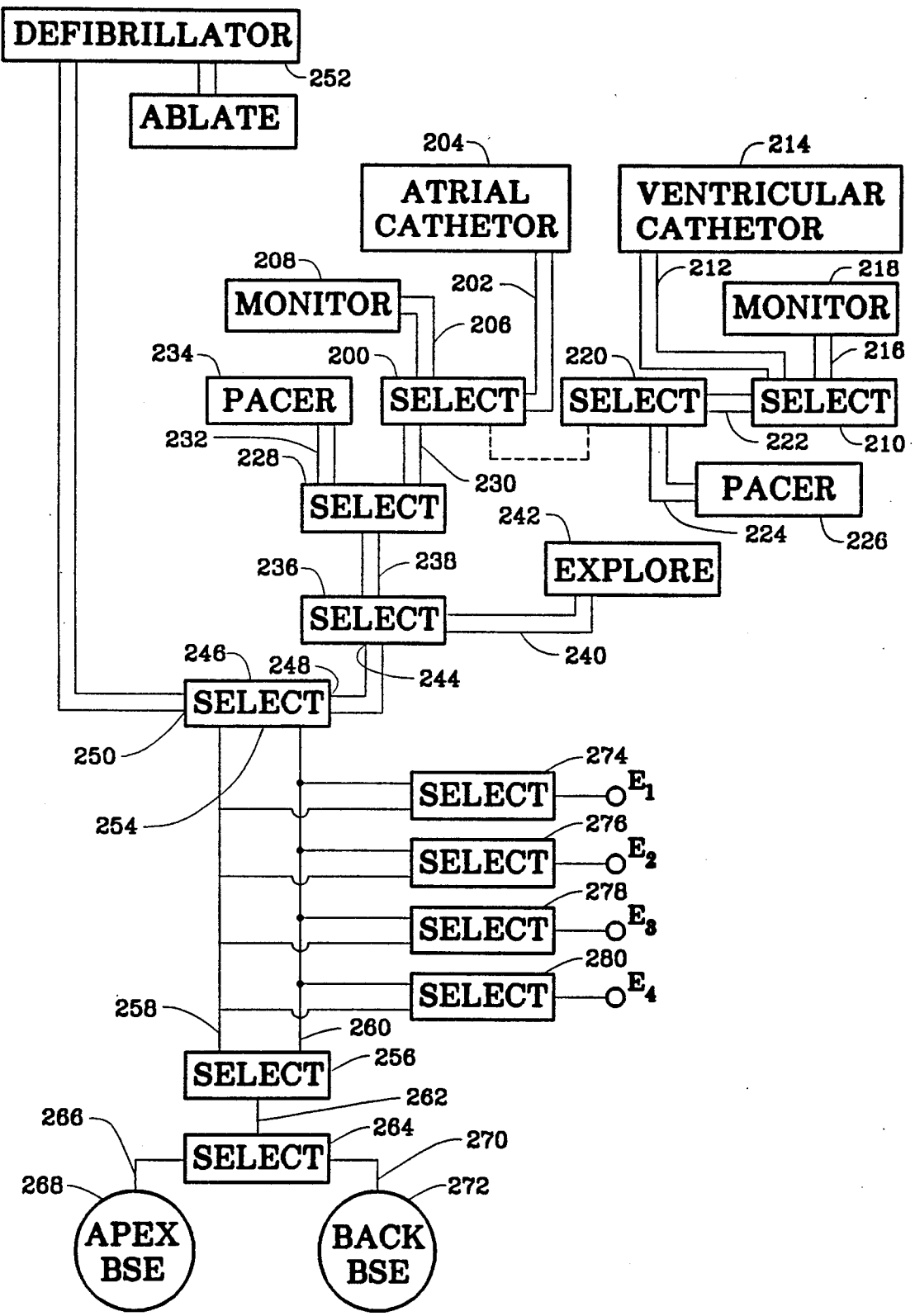
FIG. 3 is a block view of the switch box of the instant invention.

FIG. 3 is a block diagram of the instant invention wherein the switch box includes an atrial catheter electrical switch 200 having a first input 202 coupled to an atrial catheter 204 and a second input 206 coupled to a first monitoring device 208 for manually selecting therebetween; A ventricular catheter switch 210 having a first input 212 coupled to a ventricular catheter 214 and a second input 216 coupled to a second monitoring device 218 for manually selecting therebetween. A first pacer switch 220 having a first input 222 coupled to said ventricular catheter switch 210 and a second input 224 coupled to a first pacer 226;

A second pacer switch 228 having a first input 230 coupled to said atrial catheter switch 220 and a second input 232 coupled to a second pacer 234; a first DPDT panel mounted toggle switch 236 having a first double pole 238 coupled to said second pacer switching means 228, a second double pole 240 coupled to an electrocardiogram 242, said first DPDT switch 236 manually selecting between said first pole 238 and said second pole 240 to a first DPDT switch output 244; A second DPDT panel mounted switch 246 having a first pole 248 coupled to said output 244 of said first DPDT switch 236, a second pole coupled 250 to a defibrillator 252, said second DPDT switch manually selecting between said first DPDT switch output 244 and said defibrillator 252 to a second DPDT switch output 254;

A first SPDT panel mounted toggle switch 256 having a first input 258 coupled to one output of said second DPDT switch output 250 and a second input 260 coupled a second output of said second DPDT switch 250 said first SPDT switch 256 manually selecting between said first or second output of said second DPDT switch 250 to a single output 262 of said first SPDT switch 256; a second SPDT panel mounted switch 264 coupled to said first SPDT switch 262 output for manual selection for coupling to a first output 266 coupled to a apex body surface electrode 268 and a second output 270 coupled to a back body surface electrode 272, or isolation thereof. Panel mounted SPDT catheter electrode selector switches 274, 276, 278, and 280 are used for selecting between said first output 258 and second output 260 of said second DPDT switch 258 to the respective electrode sensors E1, E2, E3 and E4 respectfully, or for isolation thereof.

While a specific embodiment of the invention has been shown and described, it is to be understood that numerous changes and modifications thereof may be made without departing from the scope, spirit and intent of the invention, as set out in the appended claims.

What is claimed is:

1. A switch box for use in a clinical setting, said switch box having a defibrillator, one or a plurality of pacers, one or a plurality of recorders, a quadripolar endocardial catheter, a body surface electrode, an atrial catheter, and a ventricular catheter, coupled thereto, said switch box comprising:

catheter switching means having a first input coupled to an atrial catheter and a second input coupled to a ventricular catheter for manually selecting therebetween to a first output;

a pacer switching means having a first input coupled to said catheter switching means and a second input coupled to a pacer for manually selecting therebetween to said first output;

a first switching means having a first polarity input coupled to said pacer switching means, a second polarity input coupled to an electrocardiogram, said first switching means connecting said first input or said second input to a first polarity output;

a second switching means having a first polarity input coupled to said first polarity output and a second polarity input coupled to a defibrillator, said second switching means connecting said first polarity input or said second polarity input to a second polarity output comprising a first output and a second output;

a third switching means having a first input coupled to said first output of said second polarity output and a second input coupled to said second output of said second polarity output, said third switching means coupling said first or second input to a third switching means output;

a fourth switching means having a first input coupled to said third switching means output, said fourth switching means having a first output coupled to an apex body surface electrode and a second output coupled to a back body surface electrode, and a means for selecting a sensor of a quadripolar endocardial catheter in combination with said third switching means output, said means for selecting allowing sensor coupling to either the first input or the second input of said third switching means.

2. The switch box according to claim 1, wherein said first switching means having a first dual polarity input coupled to said pacer and a second dual polarity input coupled to said electrocardiogram is further defined as; a first multi-wired cord having a first end coupled to said Pacer and a second end coupled to said first switching means; a second multi-wired cord having a first end coupled to said electrocardiogram and a second end coupled to said first switching means; and a means for selectively coupling one of said wires of said cored of said Pacer to respective one of said first switching means and respective one of said wires of said cord of said electrocardiogram to respective one of said first switching means, whereby upon activation of said first switching means the connection between said Pacer and said first switching means is completed and the connection between said electrocardiogram and said first switching means is broken and upon deactivation of said first switching means the connection between said electrocardiogram and said first switching means is completed and the connection between said Pacer and said first switching means is broken.

3. The switch box according to claim 2, wherein said first switch means is a double pole/double throw panel mounted toggle switch.

4. The switch box according to claim 2, wherein said fourth switch means is a single pole/double throw panel mounted toggle switch.

5. The switch box according to claim 2, wherein said means for switching comprises four single pole/double throw panel mounted toggle switches.

6. The switch box according to claim 1, wherein said second switching means having a first dual polarity input coupled to said defibrillator and a second dual polarity input coupled to said first switching means is further defined as a first multi-wired cord having a first end coupled to the defibrillator and a second end coupled to said second switching means; a second multi-wired cord having a first end coupled to said first switching means and a second end coupled to said second switching means; and a means for selectively coupling one of said wires of said cord of said defibrillator to respective one of said second switching means and respective one of said wires of said cord means of said first switching means to respective one of said second switching means, whereby upon activation of said second switching means the connection between said defibrillator and said second switching means is completed and the connection between said first switching means and said second switching means is broken and upon deactivation of said second switching means the connection between said first switching means and said second switching means is completed and the connection between said defibrillator and said second switching means is broken.

7. The switch box according to claim 6, wherein said second switch means is a double pole/double throw panel mounted toggle switch.

8. The switch box according to claim 1, wherein said third switching means having a first dual polarity input coupled to said second switching means is further defined as; a first multi-wired cord means comprising a first end coupled to the second switching means, and a second end coupled to said third switching means, said third switching means selectively coupling respective wires of said cord means to respective one of said second switching means to respective one of said third switching means, whereby upon activation of said third switching means the connection between a first contact of said second switching means and said third switching means is completed and the connection between said second contact of said second switching means and said third switching means is broken and upon deactivation of said third switching means the connection between said first contact of said second switching means and said third switching means is broken and the connection between said second contact of said second switching means and said third switching means is completed.

9. The switch box according to claim 8, wherein said third switch means is a single pole/double throw panel mounted toggle switch.

10. The switch box for use in a clinical setting, said switch box having a defibrillator, one or a plurality of pacers, one or a plurality of recorders, a quadripolar endocardial catheter, a body surface electrode, an atrial catheter, and a ventricular catheter coupled thereto, said switch box comprising:

an atrial catheter switching means having a first input coupled to an atrial catheter and a second input coupled to a first monitoring device for manually selecting therebetween to a first output;

a ventricular catheter switching means having a first input coupled to a ventricular catheter and a second input coupled to a second monitoring device for manually selecting therebetween to said first output;

a first pacer switching means having a first input coupled to said ventricular catheter switching means and a second input coupled to a first pacer;

a second pacer switching means having a first input coupled to said atrial catheter switching means and a second input coupled to a second pacer;

a first DPDT panel mounted toggle switch having a first double pole coupled to said second pacer switching means, a second double pole coupled to an electrocardiogram, said first DPDT switch manually selecting between said first pole and said second pole to a first DPDT switch output;

a second DPDT panel mounted switch having a first pole coupled to said output of said first DPDT switch, a second pole coupled to a defibrillator, said second DPDT switch manually selecting between said first DPDT switch output and said defibrillator to a second DPDT switch output;

a first SPDT panel mounted toggle switch having a first input coupled to one output of said second DPDT switch output and a second input coupled to a second output of said second DPDT switch, said first SPDT switch manually selecting between said first or second output of said second DPDT switch to a single output of said first SPDT switch;

a second SPDT panel mounted switch coupled to said first SPDT switch output for manual selection for coupling to a first output coupled to an apex body surface electrode and a second output coupled to a back body surface electrode, or isolation thereof;

a plurality of panel mounted SPDT catheter electrode selector switches for selecting between said first and second output of said second DPDT switch or for isolation thereof.

11. A controllable network of medical devices adapted to be connected to patients' for coordinating the monitoring and administering of patient stimulation comprising: a switch box coupled to aid networking a defibrillator, a plurality of pacers, a plurality of recorders, a quadripolar endocardial catheter, a body surface electrode, an atrial catheter, a ventricular catheter, for coordinating and monitoring administration stimulation to each of said patients.

* * * * *